(12) United States Patent
Park et al.

(10) Patent No.: US 12,661,453 B2
(45) Date of Patent: Jun. 23, 2026

(54) MULTI-DOSE AUTO-INJECTOR FOR MANUALLY DISPENSING MULTIPLE DISCRETE DOSES OF A DRUG

(71) Applicants: Seyeon Park, New York, NY (US); Joshua Ashvil, Forest Hills, NY (US)

(72) Inventors: Seyeon Park, New York, NY (US); Joshua Ashvil, Forest Hills, NY (US)

( * ) Notice: Subject to any disclaimer, the term of this patent is extended or adjusted under 35 U.S.C. 154(b) by 21 days.

(21) Appl. No.: 18/790,719

(22) Filed: Jul. 31, 2024

(65) Prior Publication Data

US 2026/0034310 A1    Feb. 5, 2026

(51) Int. Cl.
*A61M 5/20* (2006.01)
*A61M 5/315* (2006.01)

(52) U.S. Cl.
CPC ...... *A61M 5/31593* (2013.01); *A61M 5/2033* (2013.01); *A61M 5/31548* (2013.01)

(58) Field of Classification Search
CPC ............ A61M 5/2033; A61M 5/31593; A61M 5/31548; A61M 5/2448; A61M 5/31596; A61M 5/284; A61M 5/3294; A61M 2005/1585; A61M 2005/14268; A61M 5/14244; A61M 5/20; A61M 5/24; A61M 5/3129; A61M 2005/2073; A61M 2005/208
See application file for complete search history.

(56) References Cited

U.S. PATENT DOCUMENTS

| | | | |
|---|---|---|---|
| 8,870,827 B2 | 10/2014 | Young et al. | |
| 9,022,997 B2 * | 5/2015 | Chung .............. | A61M 37/0015 604/173 |
| 9,180,252 B2 | 11/2015 | Gelblum et al. | |

(Continued)

FOREIGN PATENT DOCUMENTS

EP          0338797 A2    10/1989

OTHER PUBLICATIONS https://cooper.edu/engineering/news/invention-factoryr-2022-winners-selected, Invention Factory® 2022 Winners Selected, Sep. 6, 2022, The Cooper Union (Year: 2022).*

(Continued)

*Primary Examiner* — Bhisma Mehta
*Assistant Examiner* — Anna E Vargas
(74) *Attorney, Agent, or Firm* — Kane Kessler, P.C.; Barry E. Negrin

(57)          ABSTRACT

A manual multi-dose auto-injector structured to manually dispense multiple discrete doses of a drug is provided with a hollow housing having at least a first housing end and a second housing end. An at least partially compressible vial is disposed in the housing and contains multiple doses of the drug. The vial is in mechanical communication with both housing ends. Each housing end has a needle spring-biasedly disposed in an unactivated configuration and disposed at least partially protruding from the housing end in an activated configuration. Each needle is manually selectively in fluid communication with the vial. Pressing a housing end against a user's body causes its respective needle to move from the unactivated configuration to the activated configuration and compresses the vial to dispense a dose of the drug. Each end/needle operates independent of the other. Post-injection, each needle is locked within the housing.

15 Claims, 16 Drawing Sheets

(56)                    References Cited

U.S. PATENT DOCUMENTS

| 2013/0158474 | A1* | 6/2013 | Sullivan | ................. | A61M 11/06 |
| | | | | | 604/68 |
| 2015/0141934 | A1 | 5/2015 | Gardner et al. | | |
| 2024/0207525 | A1* | 6/2024 | Consolaro | ............. | A61M 5/508 |

OTHER PUBLICATIONS https://inventionfactory.org/inventions/nepipen, Nepipen, Mar. 22, 2023, Invention Factory, Youtube: https://www.youtube.com/watch?v=SDAmOZ2tCrg (Year: 2023).*

* cited by examiner

19

15

17

33

27

20

27

33

22

MULTI-DOSE AUTO-INJECTOR FOR MANUALLY DISPENSING MULTIPLE DISCRETE DOSES OF A DRUG

BACKGROUND OF THE INVENTION

Field of the Invention

The invention is related to devices for treating anaphylaxis and preventing progression to life-threatening respiratory and/or cardiovascular symptoms and signs. More specifically, the invention is related to portable auto-injectors for manually dispensing multiple discrete doses of a drug such as epinephrine.

Description of Related Art

One in 50 Americans experiences anaphylaxis, a severe allergic reaction that can lead to death in a short period of time; in severe cases, within 15 minutes. In 2015, 3.6 million Americans were prescribed an epinephrine auto-injector due to anaphylactic shock. Medical doctors prescribe two epinephrine injectors at a time and recommend both always to be carried since one dose is sometimes not enough, especially for food allergies. In fact, 16-35% of cases of anaphylaxis shock required a second dose of epinephrine. Also, carrying two epinephrine auto-injectors can help deal with biphasic anaphylaxis, a second anaphylactic reaction followed by an asymptomatic period ranging from 1 to 72 hours in the absence of further exposure to the triggering antigen. Incidence of biphasic anaphylaxis occurs in up to 23% of adults and 11% of children. Despite this, 82% of epinephrine auto-injector users do not carry two injectors.

Consequently, 45% of emergency care visits for severe allergic reactions were because of the unavailability of a second dose. There are several reasons why people do not carry a second dose. First, existing epinephrine auto-injectors are too bulky. Second, some people do not know the importance of the second dose. Third, some people do not necessarily want to carry two identical products.

An epinephrine auto-injector called Epipen (NDC 49502-500, NDC 49502-501 for Epipen Jr, both marketed by MYLAN of Cannonsburg, PA) is used worldwide. However, the Epipen is bulky—about 6 inches in length and 1 inch in width. A significant issue with the Epipen is that the safety cap is on the opposite side of the needle. This leads users to believe that the side with the needle has an activating button, which leads to the needle injecting into their thumb. As a result, the person in shock cannot get their dose of epinephrine and is injured as well. Also, the Epipen must be jabbed onto the injection site with the user's force and aim. In some cases, the user fails to aim the injector properly, and the needle severely tears through their skin. These features apply to other epinephrine auto-injectors with the same mechanism, like Jext (made by LK-Abelló of Copenhagen, Denmark) and Adrenaclick (made by Impax Laboratories, LLC of Hayward, CA).

Another conventional auto-injector is the Auvi-Q (NDC 60842-021 for 16.5 lbs to 33 lbs, NDC 60842-022 for 33 lbs to 66 lbs, NDC 60842-023 for over 66 lbs, made by Kaléo of Richmond, VA). It is made to be more compact (it is the size of a credit card, thickness of a smartphone) and more user-friendly than Epipen since it has a voice instruction activated by opening the outer safety guard. However, it is still inconvenient. The outer case can be removed easily inside a person's purse or pocket and unintentionally initiate the voice instruction. The user can stop the instruction by putting the device back on the outer case. However, users can put the safety cap back after they take it off. Then the voice instruction does not reset to the correct place, letting users miss the information when they have to use it in an emergency. The safety cap can be putted back even after injection, may cause confusion if it is used or not. Furthermore, Auvi-Q was recalled in 2015 due to the delivery of an inaccurate amount of the drug since it deploys a gas jet mechanism to inject the medication. Despite the fact that Auvi-Q came back to the market in 2017, it does not solve the cumbersomeness of carrying two identical products.

Prior double-dosed epinephrine auto injector, Twinject (NDA 020800, last marketed by Shionogi Inc. of Florham Park, NJ), was discontinued in 2015 due to safety reasons. The second dose was provided by disassembling the whole device, taking the syringe out, and injecting the precise amount by the users themselves.

Lastly, U.S. Pat. No. 9,180,252 to Gelblum et al. discloses a bellows syringe fluid delivery system. This injector uses a pneumatic air piston to compress a bellow syringe filled with the medication that is being injected. This device utilizes electronics to deliver injections accurately and with proper force. However, this device is not meant to be used as a compact and intuitive auto-injector. It is intended for a medical setting where it would be used by trained personnel, not an emergency situation where an individual is in shock.

The common shortcoming of existing epinephrine auto-injectors is that only 16% of patients prescribed an epinephrine auto-injector could correctly demonstrate its use.

Thus, there is a long-felt need for a safe, compact, double-dosed, and intuitive and easy to use epinephrine auto-injector that ensures that patients are prepared for an unexpectable, life-threatening allergic reaction.

SUMMARY OF THE INVENTION

The above and other objects are fulfilled by the invention, which is a manual multi-dose auto-injector structured to manually dispense multiple discrete doses of a drug. It includes a hollow housing having at least a first housing end and a second housing end, and an at least partially compressible vial disposed in a central portion of the housing adapted to contain multiple doses of the drug to be dispensed, the vial in mechanical communication with the first housing end and the second housing end. A first needle is spring-biasedly disposed substantially in the first housing end in a first unactivated configuration and disposed at least partially protruding from the first housing end in a first activated configuration, the first needle manually selectively in fluid communication with the vial. A second needle is spring-biasedly disposed substantially in the second housing end in a second unactivated configuration and disposed at least partially protruding from the second housing end in a second activated configuration, the second needle manually selectively in fluid communication with the vial. Pressing the first housing end against a user's body causes the first needle to move from the first unactivated configuration to the first activated configuration and compresses the vial to a first extent such that a first dose of the drug is dispensed from the first needle to the user. Similarly, pressing the second housing end against a user's body causes the second needle to move from the second unactivated configuration to the second activated configuration and compresses the vial to a second extent such that a second dose of the drug is dispensed from the second needle to the user.

Preferably, the inventive auto-injector further includes a first spring-biased co liar engaging a first end of the vial, the first spring-biased collar being locked in a first proximal position via a first locking mechanism in the first unactivated configuration and pushed into a distal position in the first activated configuration when the first locking mechanism is unlocked. A second spring-biased collar is also provided engaging a second end of the vial, the second spring-biased collar being locked in a second proximal position via a second locking mechanism in the second unactivated configuration and pushed into a distal position in the second activated configuration when the second locking mechanism is unlocked. Optionally, the invention includes a first central spring biasing the first spring-biased collar and a second central spring biasing the second spring-biased collar.

Optionally, each of the first and second locking mechanisms mentioned above respectively include: an end ring disposed at the distal end of the housing end; at least one prong proximally extending from the end ring towards the collar; and at least one radial plunger spring-biased into a locking space formed in the housing in the unactivated configuration and pushed into an activation space in the collar in the activated configuration. Pressing the housing end against a user's body causes the end ring to push a proximal prong end of the at least one prong proximally into contact with the at least one radial plunger, thereby pushing the at least one plunger out of the locking space in the housing and into the activation space in the collar.

Preferably, after the first dose is dispensed, the first needle moves from the first activated configuration to a first deactivated configuration, and after the second dose is dispensed, the second needle moves from the second activated configuration to a second deactivated configuration.

Optionally, each of the first and second locking mechanisms respectively further includes at least one plunger retraction slot formed in the housing distally from the locking space. After the dose is dispensed, the at least one radial plunger is spring-biased into the at least one plunger retraction slot, and the needle is in a deactivated configuration. Optionally, the collar is spring-biased proximally and the needle is withdrawn proximally back into the housing in the deactivation configuration.

Preferably, the vial includes a first compressible region corresponding to the first dose and a second compressible region corresponding to the second dose. Optionally, the first compressible region includes bellows structured to fold when compressed and thereby force the first dose out of the vial and the first needle, and the second compressible region includes bellows structured to fold when compressed and thereby force the second dose out of the vial and the second needle. Optionally, the first compressible region includes bellows structured to fold when compressed by the first spring-biased collar and thereby force the first dose out of the vial and the first needle, and the second compressible region includes bellows structured to fold when compressed by the second spring-biased collar and thereby force the second dose out of the vial and the second needle.

The drug in question is optionally epinephrine.

Preferably, the end ring remains proximally pushed in the deactivated configuration to provide a visual indication that the respective injection has occurred.

The need for a two-dosed, compact, safe, and intuitive epinephrine auto-injector addressed above is met by the invention. The invention uses an entirely mechanical, spring-loaded mechanism for injection. It has two sides, in which each dose would come out of one end. To prevent cross contamination, each side has its own needle having a plug valve. In addition, one common vial of fluid is used. It is an at least partially compressible vial having bellows that, when compressed, ejects out a certain amount of fluid (e.g., one dose). The one-vial mechanism is important for making the overall device compact, as there are fewer total parts needed to create the mechanism. Moreover, the device has a very user-friendly system for activation. All the user has to do is slide off a safety cap and push the device into their outer thigh. After the drug is delivered, the device retracts and deactivates the needle on its own.

The structure of this device involves a system of springs, which work in cooperation to allow the drug to be delivered and the needle to be retracted. The central vial itself has two ends, both of which are needles having plug valves. The vial is centered within the device using two low-force springs on either end, which hold the vial in the space between them. In the very center of the device, there are two high-force springs in a compressed state. These springs are engaged and disengaged through a longitudinal prong system. The prongs slightly stick out of the end of the casing and have a sizeable ring connecting them, so that when they impact the skin, they do not have the possibility of bending. When impacted by the force of the user's thigh, the prongs are pushed into the casing. The prongs push against small spring-loaded lateral/radial plungers attached to the strong spring, which hold it in its compressed state. When these plungers get pushed, instead of holding the spring to the casing, they attach the spring to the vial, allowing it to move forward and the needle to be unsheathed. Then, after the needle is unsheathed from the casing and the 0.3 mL of a drug is injected (one dose), this high-force spring disengages from the bellow, as the plungers have another opening within the casing, allowing them to return to their original state. This allows the retraction mechanism to begin. The low-force springs mentioned before do not just serve the role of aligning the bellow; they also push the bellow back into its original position.

Each of these springs is connected from the end of the case to one end of the vial. So, when the high-force spring is no longer in contact with the vial, the low force spring can begin pushing the bellow back into its original position, which ensures that the vial is aligned properly for the next injection and the needle is no longer exposed. The disengagement of the high force spring also ensures that the side that was injected could not be used again, as the spring propelling the vial forward is no longer in a compressed position where it could propel the vial forward upon reactivation on that same side. If the user is still in shock 5-15 minutes after their first dose, they can flip the device around, and the same process will be repeated using the other end.

This invention has needles in the same direction as the safety cap to help users intuitively recognize which side releases the dose of medication. In addition, the safety cap utilizes a sliding mechanism to be easily removed.

With this invention, users can place the auto-injector onto the injection site first and then push it with ease, which helps users to use it correctly and safely. After the injection, the needle is automatically retracted, and the hole that the needle comes out of is small enough to prevent the user's finger from being inserted.

The invention also prevents contamination of the medication. The needles are not reused, and the plug valve automatically closes the path from the needle to the vial right after injection. This allows for no negative pressure to be formed, ensuring that neither blood nor air bubbles will be drawn inside the vial.

DETAILED DESCRIPTION OF THE INVENTION AND DRAWINGS

Figure 1A:
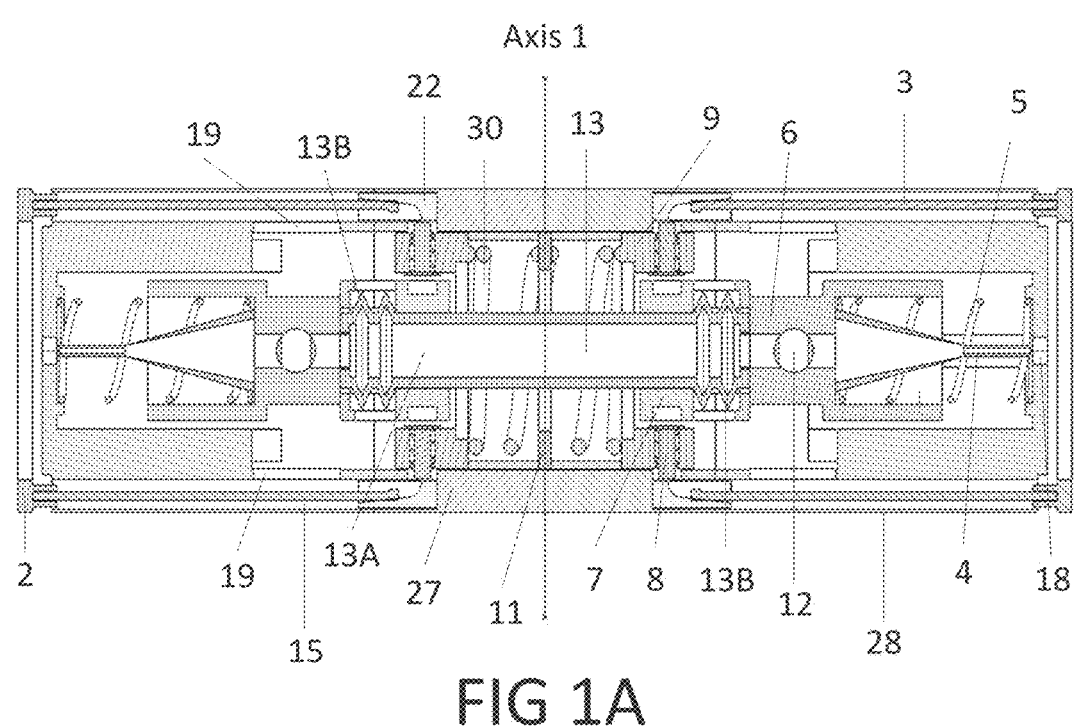
FIG. 1A is a front side sectional view of the auto-injector in an inactivated state in accordance with an embodiment of the invention.
Figure 1B:
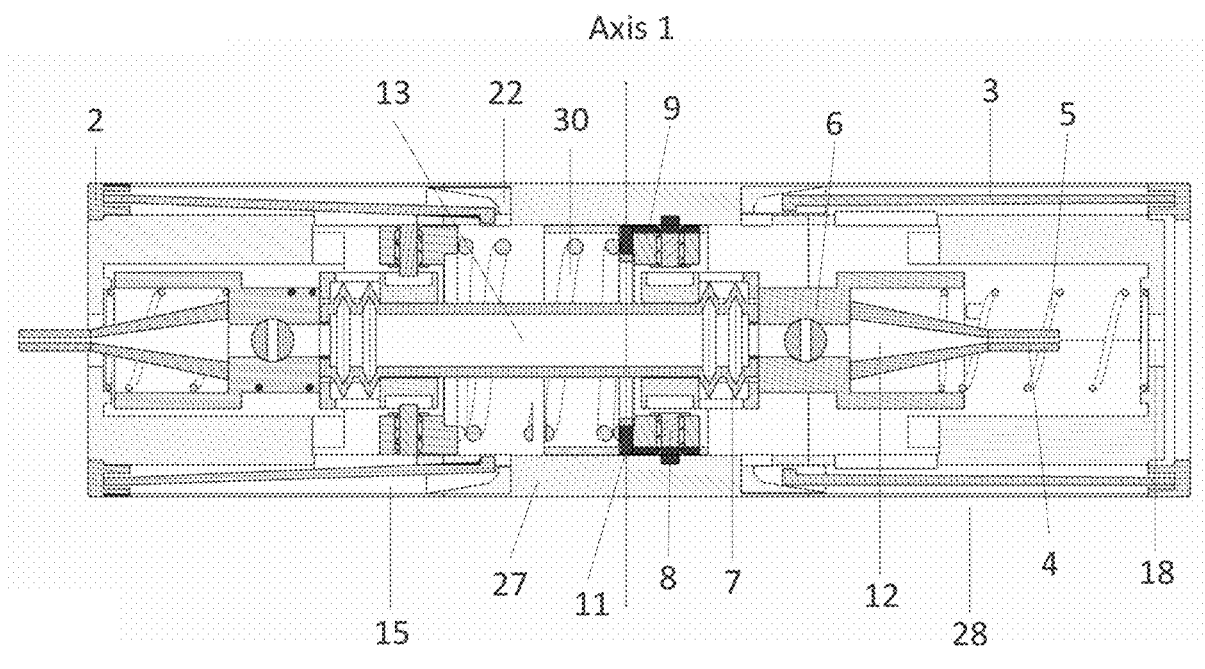
FIG. 1B is a front side sectional view of the auto-injector in an activated state in accordance with an embodiment of the invention.
Figure 2:
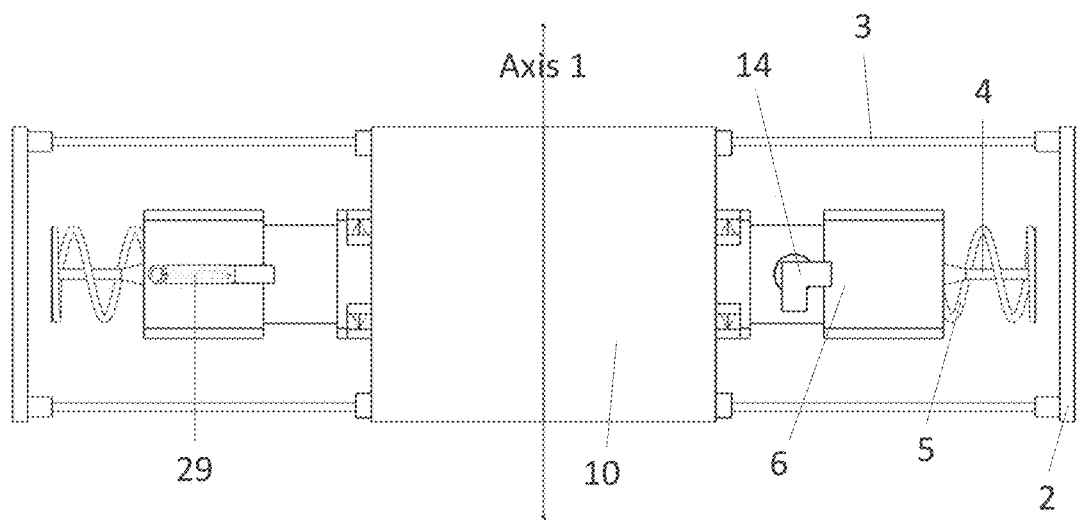
FIG. 2 is a front side view of the auto-injector of FIG. 1 without a case in an inactivated state. The auto-injector is symmetrical about axis 1.

Description will now be given with reference to the attached FIGS. 1-17. It should be understood that these figures are exemplary in nature and in no way serve to limit the scope of the invention, which is defined by the claims appearing herein below.

Reference is made herein to the terms "proximally" and "distally". In the context of the invention, "proximally" means "in towards the longitudinal center of the device", and "distally" means "outwards away from the longitudinal center of the device".

The invention is a two-dose epinephrine auto-injector 34 utilizing a single, common vial 13. Vial 13 is at least partially compressible. It includes a central section 13A and bellows 13B at each end. The vial 13 is connected to two needles 4, one on each end. The device is activated by removing the safety cap 1 and pushing one end of the stabilization ring 2 on the user's outer thigh. When this occurs, a high force compression spring 30 is activated as described below. Needle 4, which is connected to vial 13 at bellows 13B, is pushed out of the closing case 28, penetrating the user's skin. The high force compression spring 30 then compresses at least bellows 13B of vial 13, injecting the medicine. Lastly, the high force compression spring 30 is disengaged as described below, allowing a low-force compression spring 5, initially providing negligible force, to move vial 13 and needle 4 back to their original position. If a second dose is needed, injection using needle 4 on the opposite side of the auto-injector 34 can be done in the same order.

Figure 6A:
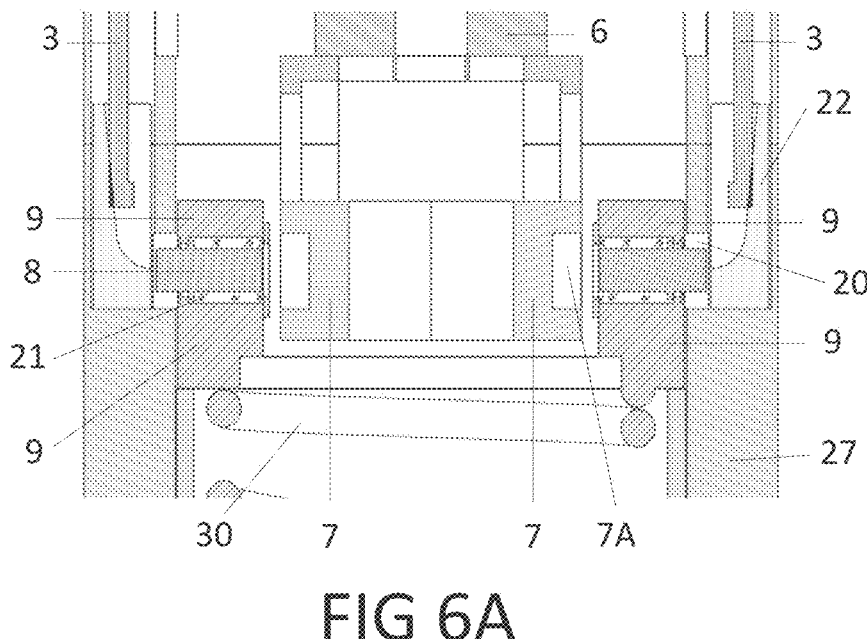
FIG. 6A is an enlarged front side sectional view of an auto-injector in accordance with an embodiment of the invention illustrating the position of the plunger, plunger spring, and the prong in an inactivated state.
Figure 6B:
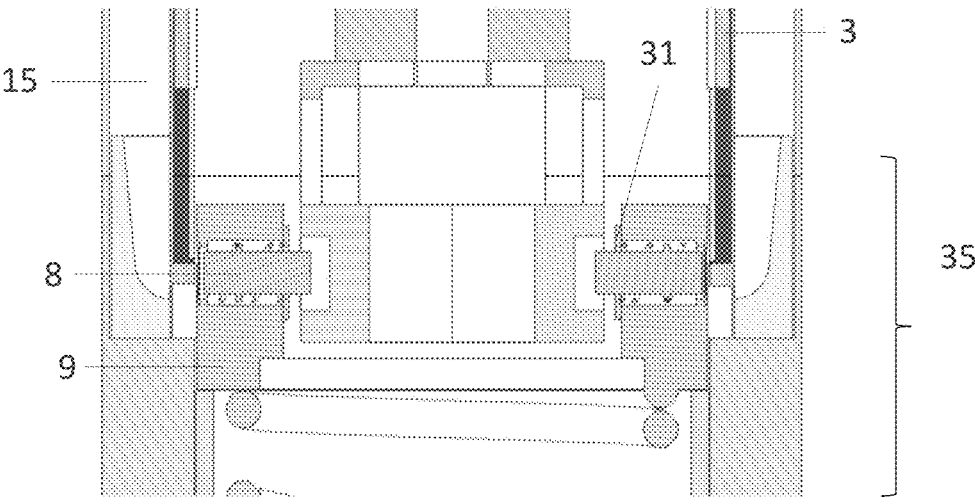
FIG. 6B is an enlarged front side sectional view illustrating the auto-injector of FIG. 6A with the position of the plunger, plunger spring and the prong in an activated state.
Figure 6C:
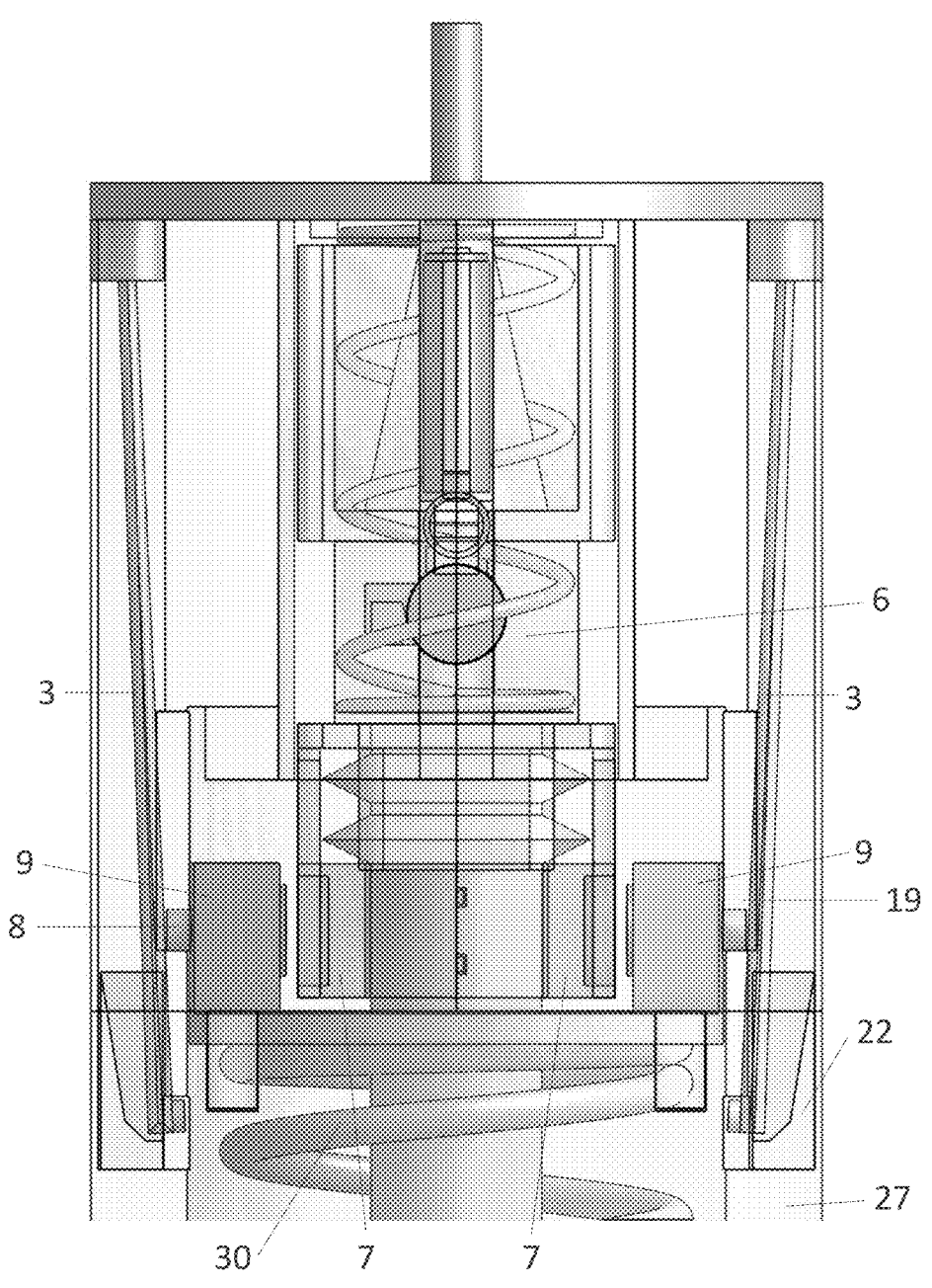
FIG. 6C is an enlarged sectional view illustrating the auto-injector of FIG. 6A with the position of the plunger, plunger spring and the prong in a deactivated state.
Figure 6D:
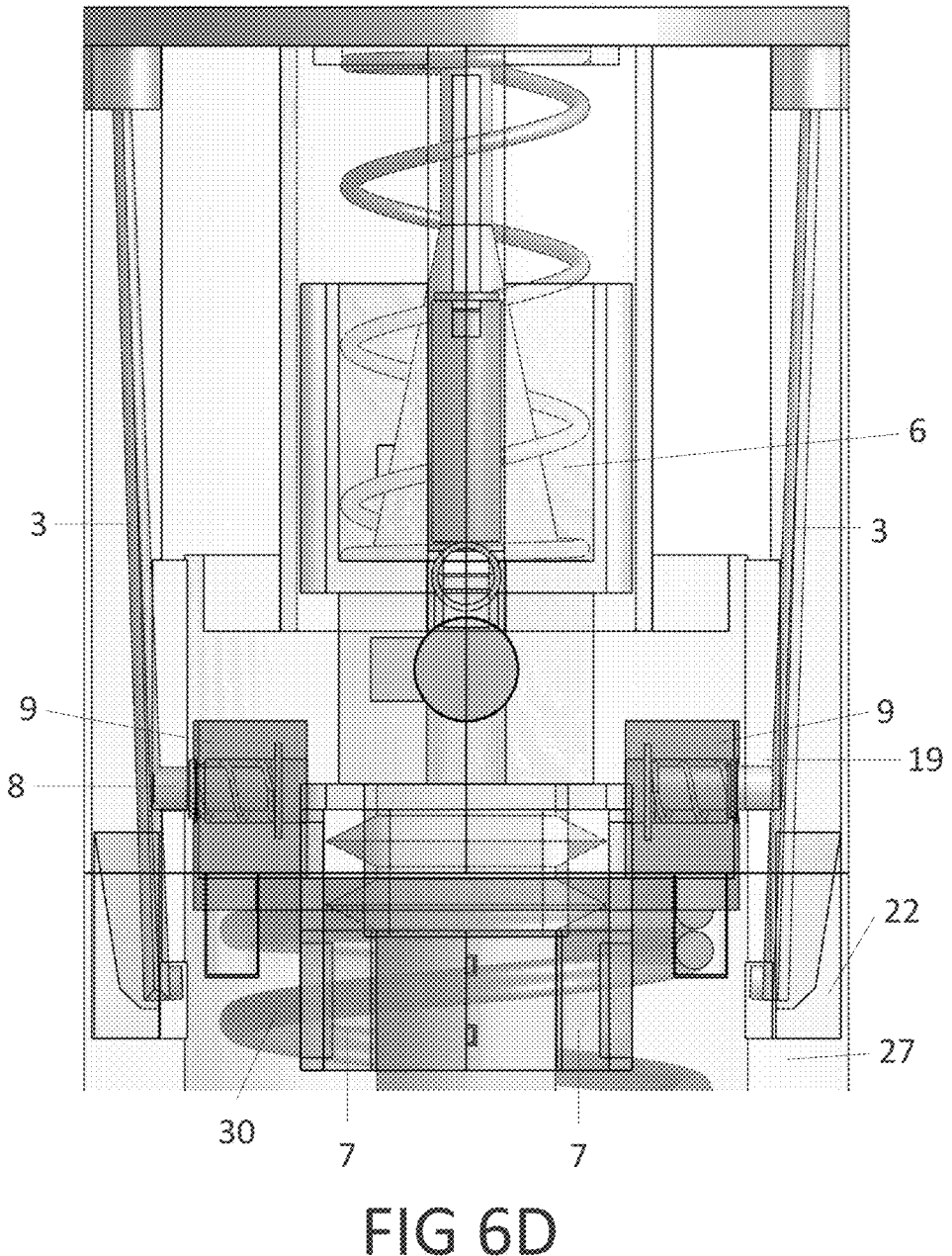
FIG. 6D is an enlarged sectional view illustrating the auto-injector of FIG. 6A with the high-force spring 30 disengaged from the vial in the deactivated state.
Figure 7:
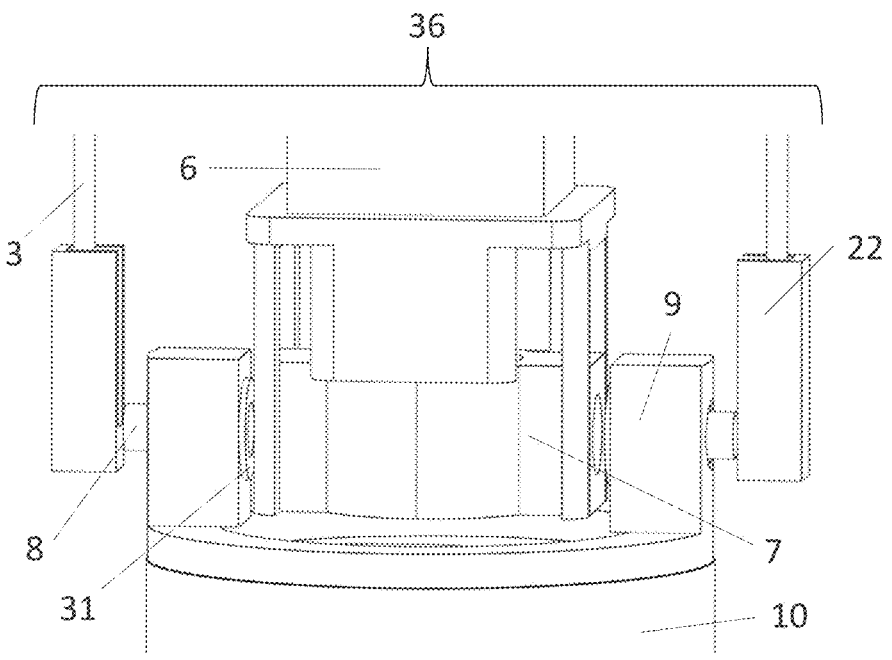
FIG. 7 is a front side perspective view of FIG. 6A from above.
Figure 8A:
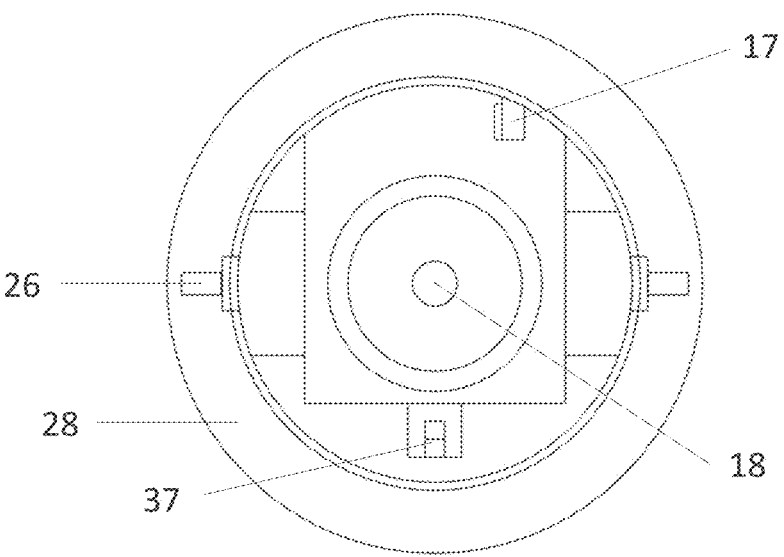
FIG. 8A is a top view of the assembled closing case of the auto-injector.
Figure 8B:
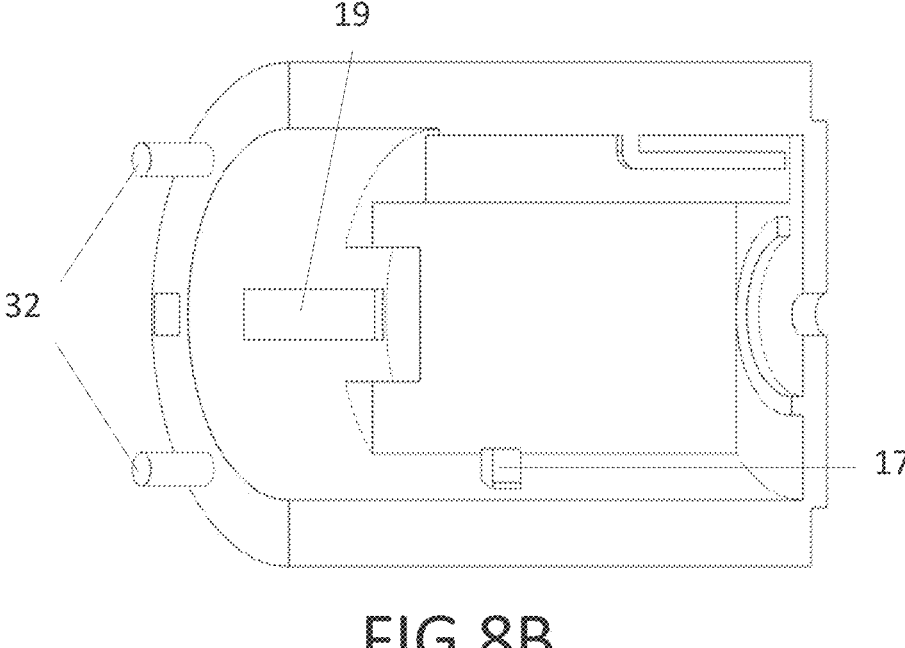
FIG. 8B is a right-side perspective view of the left closing case from above.
Figure 8C:
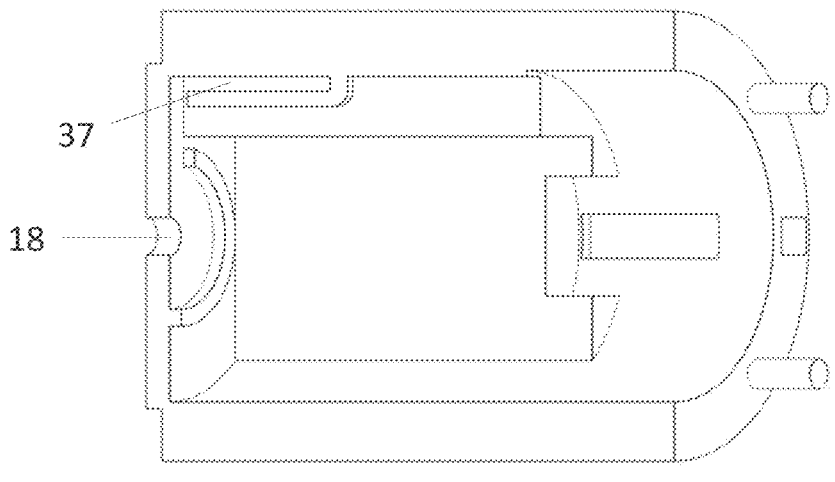
FIG. 8C is a left side perspective view of the right closing case from above.
Figure 8D:
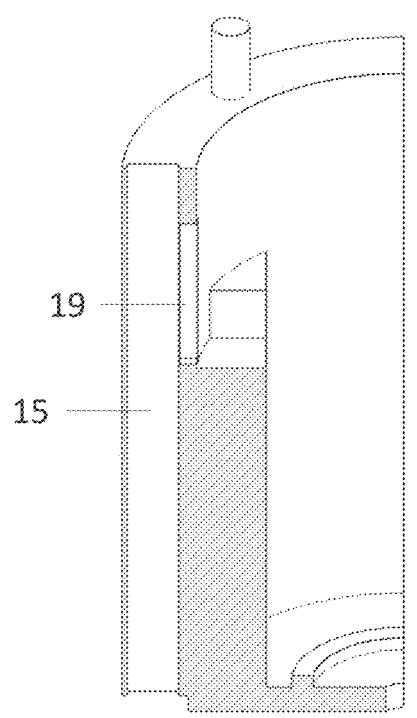
FIG. 8D is a front perspective sectional view of the closing case from above.
Figure 8D:
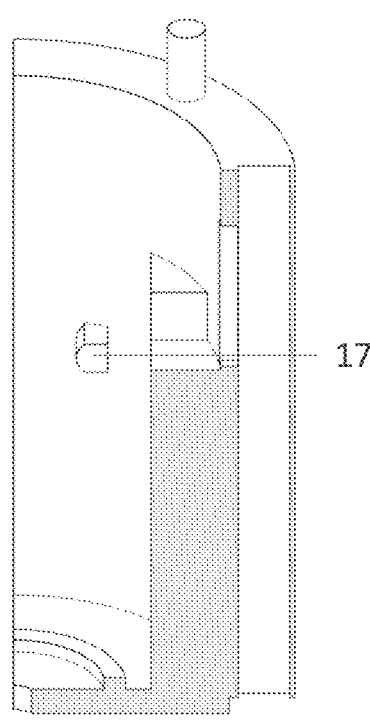

Auto-injector 34 includes two subassemblies: activated complex 35 and center complex 36. The activated complex 35 includes the plunger housing 9, lateral plunger 8, the plug valve 6, the needle 4, and the collar 7 as shown in FIGS. 6A-D. The center complex 36, shown in FIG. 7, is a subassembly of the plunger housing 9, high force compression spring 30, metal plate 11 and the spring housing 10, which are attached to each other.

Figure 3:
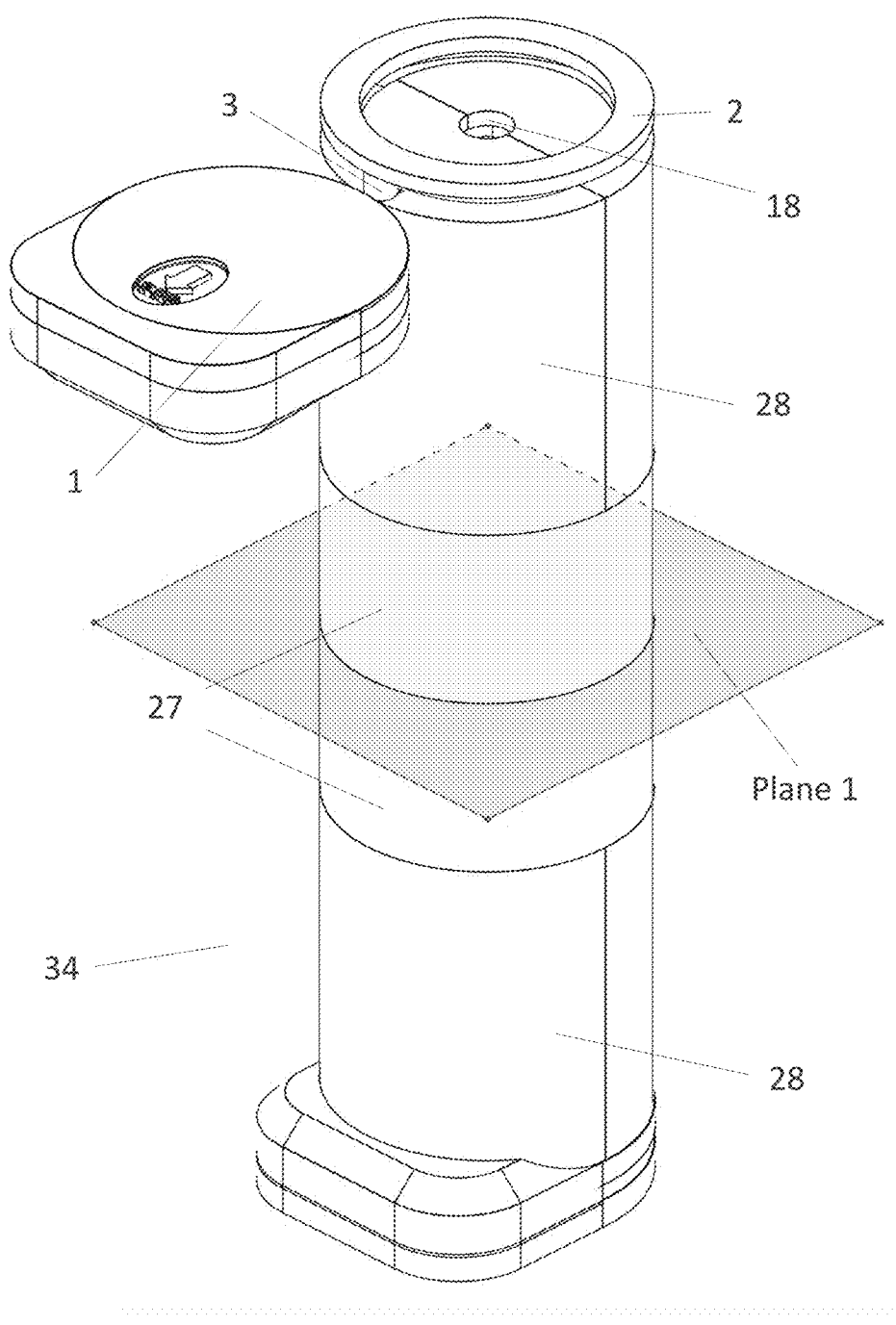
FIG. 3 is a front perspective schematic view of an auto-injector in accordance with an embodiment of the invention. The auto-injector is symmetrical about plane 1.
Figure 4A:
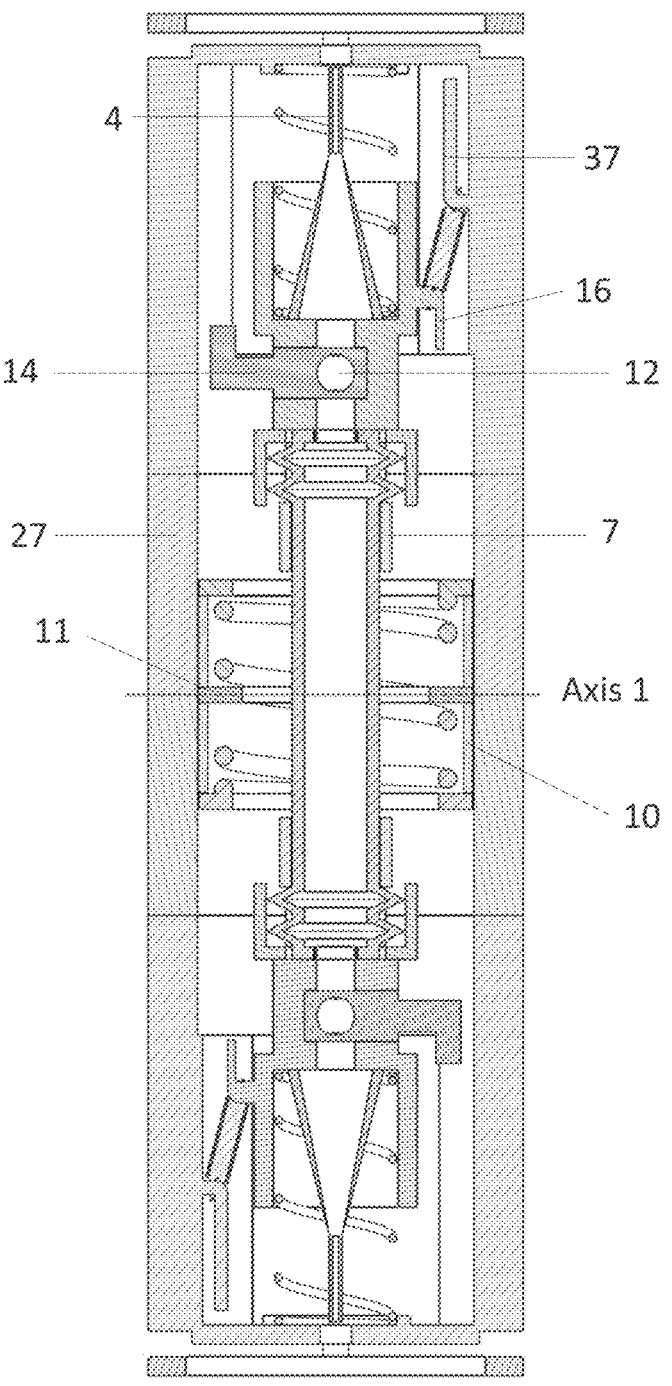
FIG. 4A is a right-side sectional view of the auto-injector of FIG. 1 in an inactivated state.
Figure 4B:
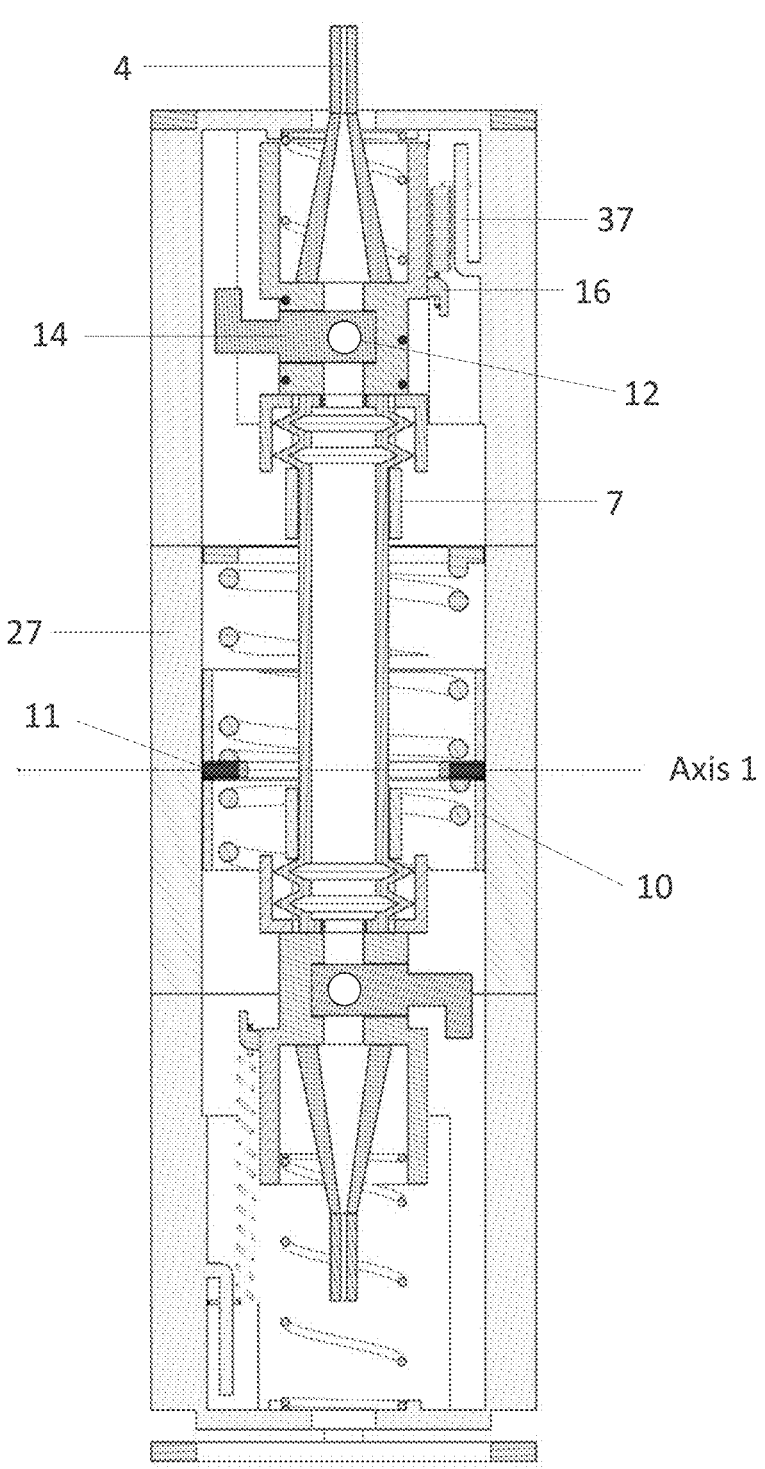
FIG. 4B is a right-side sectional view of the auto-injector of FIG. 1 in an activated state.
Figure 5:
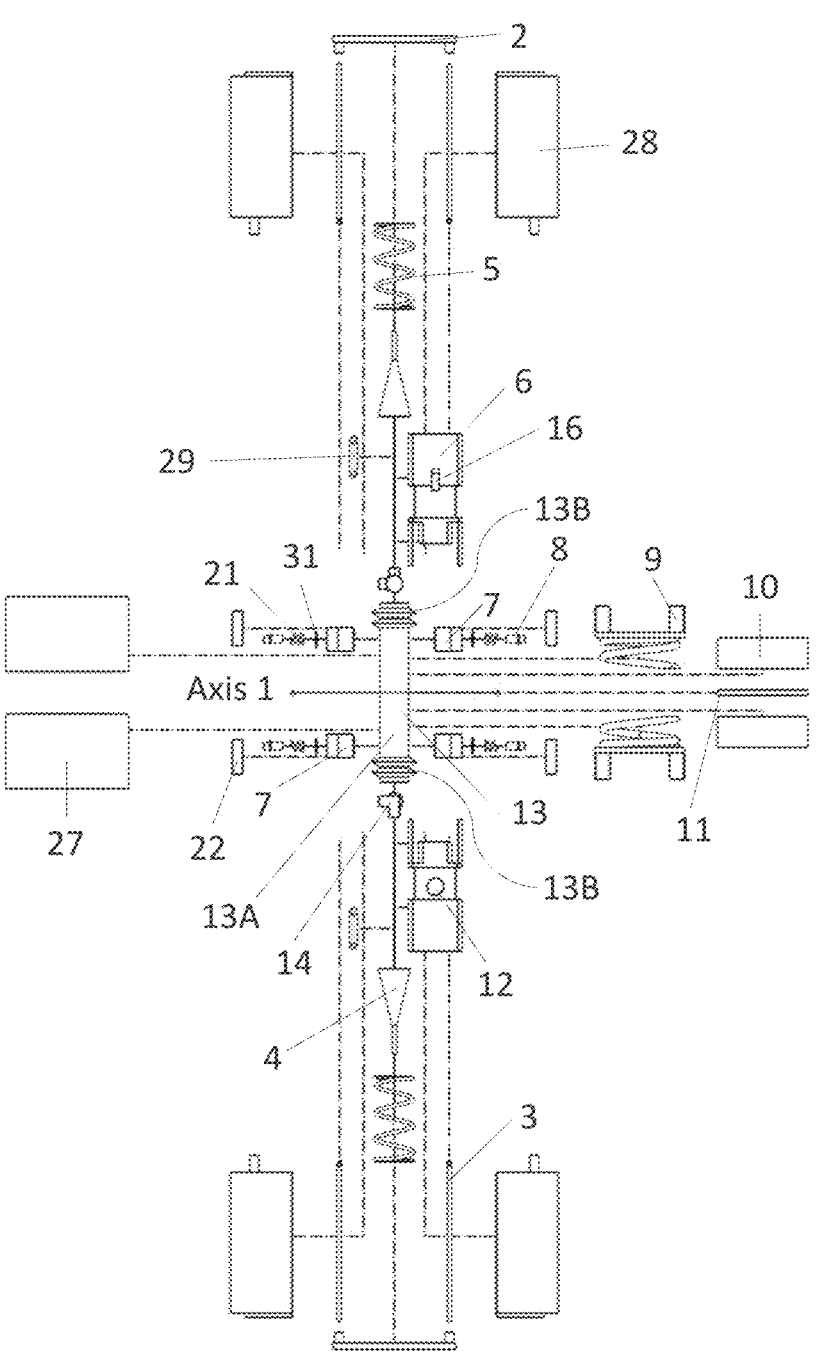
FIG. 5 is a front side exploded view of the auto-injector of FIG. 1.

The dose can be stored in liquid form. The outer case is shown in FIGS. 8A-8D and 9A-9B. The outer case is an assembly of the left and right closing case 28 and the middle case 27. The assembly of the middle case 27 and the closing case 28 utilizes a press-fit mechanism by engagement of the assembly stud 32 and assembly hole 33. The outer case has a cylindrical shape, which is ergonomically sized to permit easy grasping and use by the user or caregiver. The middle case 27 and spring housing 10 can have a small circle window which allows users to check the color of the medication to see whether it is spoiled or not. The closing case 28 has a needle hole 18 formed at the end that is sized to inject the needle 4. When in place, the safety cap 1 prevents inadvertent use or activation of the auto-injector 34. The safety cap 1 is illustrated in FIG. 3. The stabilization ring slot 25 of the safety cap 1 holds the stabilization ring 2 when the auto-injector 34 is in an inactivated state. The prongs are surrounded by the prong slot 26 of the safety cap 1 in an inactivated state.

Figure 17:
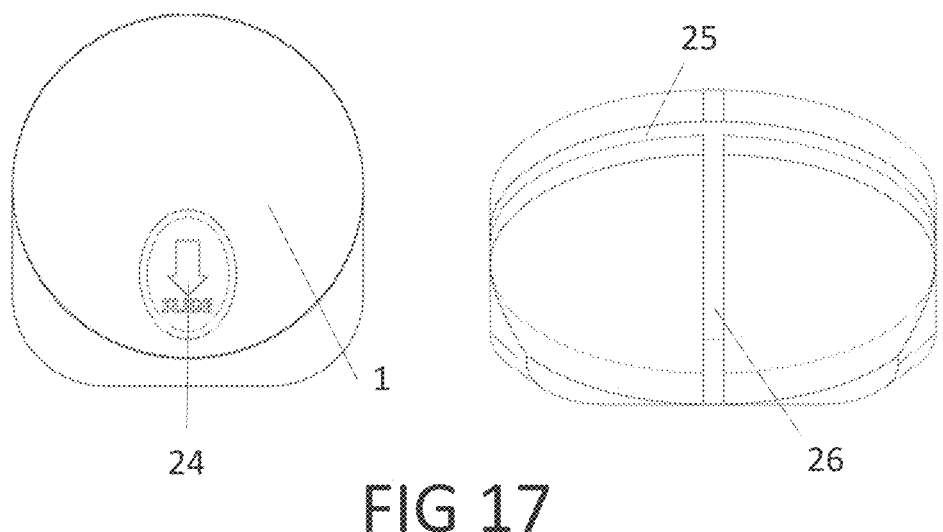
FIG. 17 is a top view and rear perspective view from the bottom of the safety cap.

The first step of activating the auto-injector 34 is sliding off one of the safety caps 1 from one side to be used. FIG. 3 illustrates how the cap slides off of the device, and FIG. 17 depicts how it slides directly onto stabilization ring 2. The finger instruction 24 helps users to intuitively recognize the way to remove the safety cap 1. Then, the user grabs the outer case 27 and 28 and places the stabilization ring 2 on their outer thigh. The final step of activating the auto-injector 34 is pushing the stabilization ring 2 onto the outer thigh. When turning to FIGS. 1 and 2, it is shown that the two prongs 3 are attached below the stabilization ring 2 at a 180-degree angle to the center of the stabilization ring 2. The stabilization ring 2 ensures a stable and even force applied to the prongs. Prong 3 is extended downwardly along the opposite side of the closing case 2. The stabilization ring 2 remains pushed in after activation, which helps the users recognize whether the side is used or not. In addition, another indicator of a side being used is the safety cap 1 being removed.

Figure 9A:
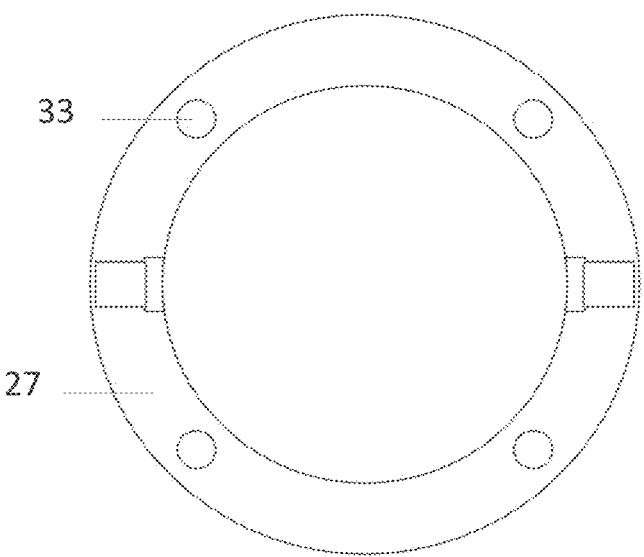
FIG. 9A is a top view of the middle case of the auto-injector.
Figure 9B:
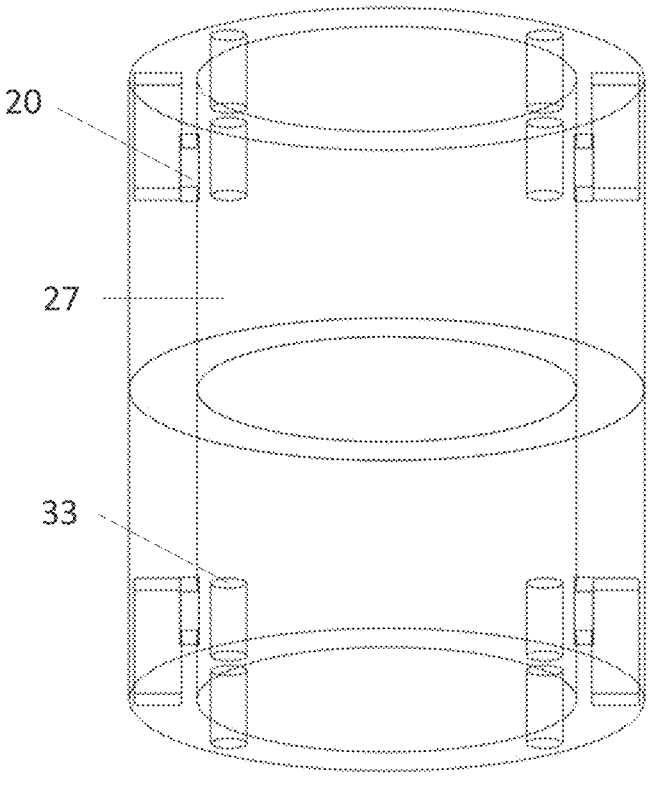
FIG. 9B is a front perspective view of the middle case from above.
Figure 10:
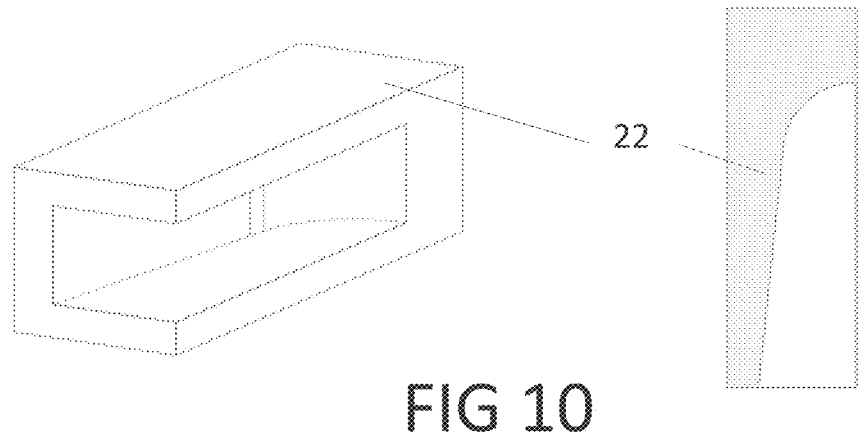
FIG. 10 is a front perspective view from above and a top sectional view of the prong guide.
Figure 11:
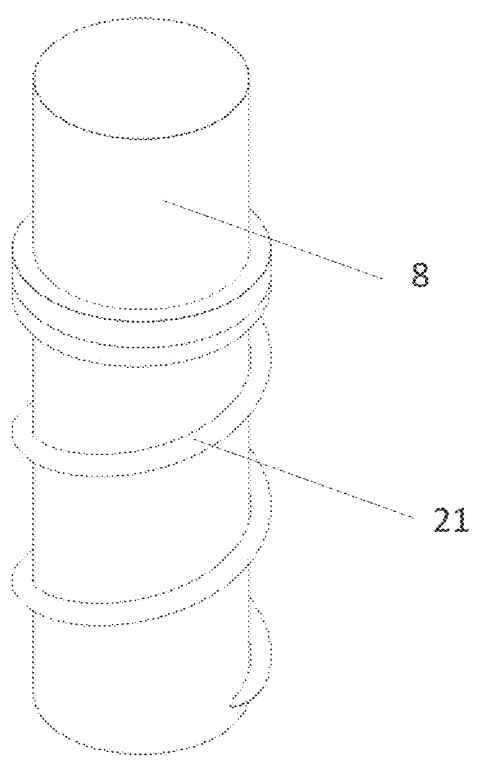
FIG. 11 is a perspective view of the plunger and the plunger spring assembly from above.
Figure 12:
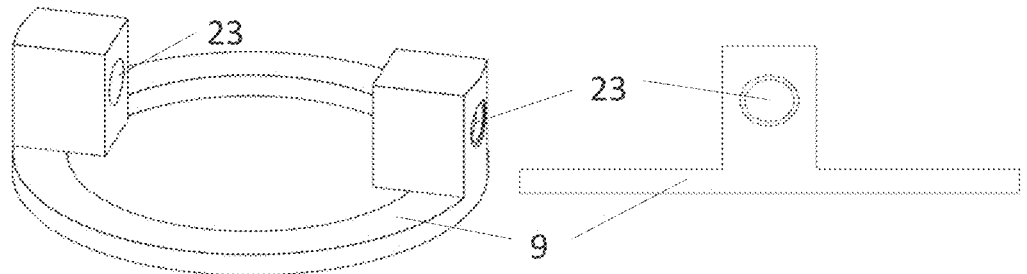
FIG. 12 is a top perspective view and left view of the plunger housing of the auto-injector.
Figure 13:
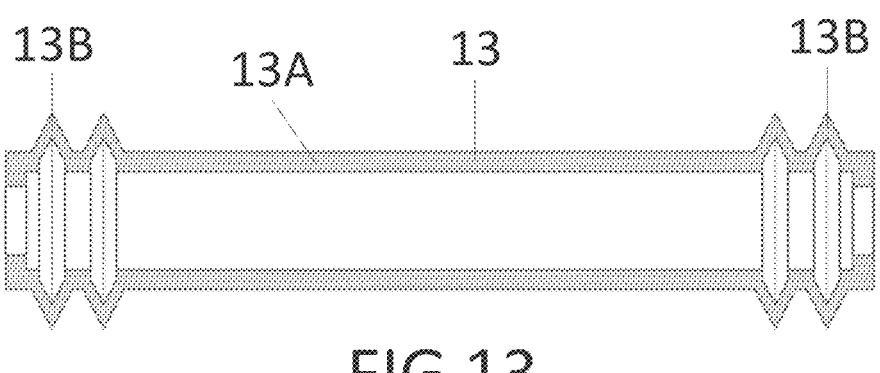
FIG. 13 is a right sectional view of the vial of the auto-injector.
Figure 14:
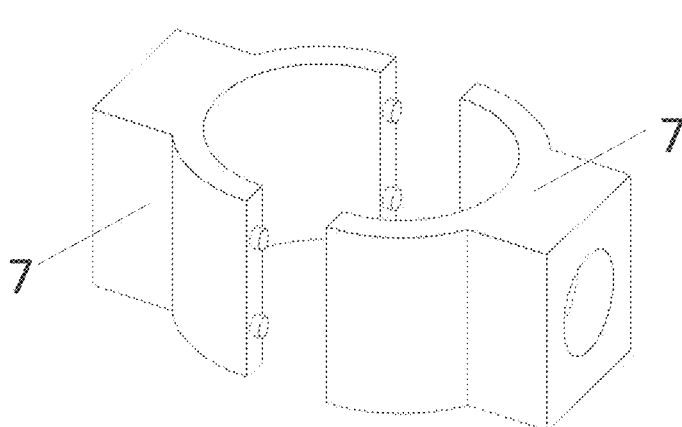
FIG. 14 is a front perspective view of the collar of the auto-injector from above.

When the stabilization ring 2 is pushed, each prong 3 slides proximally along the prong channel 15 and presses lateral plunger 8 in the plunger releasing slot 20. Prong slide 15 extends through the middle case 27 and the end case 28, and is illustrated in FIGS. 8A, 8D, 9A, and 9B. The prong guide 22, shown in FIG. 10, helps the prong 3 change the direction towards the plunger 8 so that the prong 3 presses the plunger. The process described here is illustrated in FIGS. 6A and 6B, where the auto-injector is unactivated in FIG. 6A and activated in FIG. 6B. The plunger 8 holds a high force compression spring 30 in a compressed state in the unactivated state by initially being slotted into the plunger releasing slot 20 and held there by plunger spring 21 (see FIG. 6A). The plunger releasing slot 20 is depicted in FIGS. 6A and 9B, and is a small cavity within the middle case 27 in which the plunger sits in the unactivated state. The plunger 8 is housed within plunger housing 9, which is connected to the high-force compression spring 30 (shown in FIGS. 1 and 7). Thus, with all these parts being connected, the plunger 8 being held within the plunger releasing slot 20 allows for the high force compression spring 30 to be held in a compressed state.

Figure 15A:
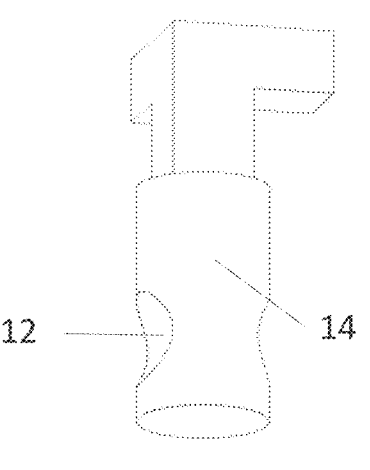
FIG. 15A is a front perspective view of the stopcock from above.
Figure 15A:
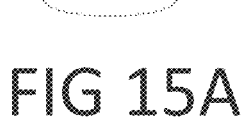
Figure 15B:
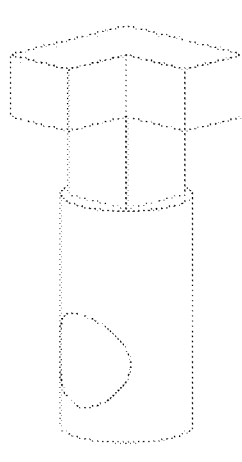
FIG. 15B is a rear perspective view of the stopcock from bottom.
Figure 16:
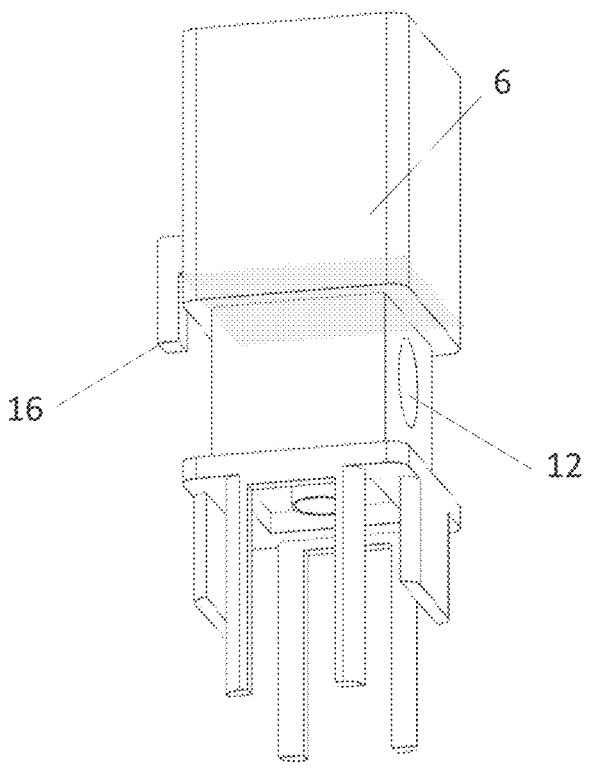
FIG. 16 is a right perspective view of the plug valve from the bottom.

When plunger 8 is pressed inside the plunger housing 9 by the prongs 3, the plunger 8 is pushed out of slot 20 and into collar slot 7A and holds the collar 7, forming the activated complex 35, illustrated in FIG. 6B. The high force compression spring 30 releases, propelling the activated complex 35 distally forward. As the activation complex 35 moves distally forward, the needle 4 moves outside the closing case 28 through the needle hole 18 and is inserted into the user's outer thigh. When needle 4 is fully inserted, the high force compression spring 30 continues to push collar 7, thereby compressing bellows 13B and rapidly releasing the medication. Once bellows 13B are fully compressed, the plunger 8 is pulled into plunger retraction slot 19 (shown in FIGS. 6C, 6D, 8B, and 8C) by plunger spring 21, thereby disengaging the high-force compression spring 30 from vial 13. The plunger 8 can be pushed into the plunger housing 9 and retracted into the plunger releasing slot 20 since the plunger spring 21 encircles the plunger 8. (See FIGS. 6A, 6B, and 11.) To prevent the plunger and plunger spring from falling out of the plunger housing 9, plunger ring 31(shown in FIGS. 5 and 6B) holds these parts in the plunger housing. Once high-force compression spring 30 is fully extended, the activation complex 35 pushes the low-force compression spring 5 (shown in FIGS. 1, 2, and 5), which automatically retracts the needle 4 after the medication is released. In addition, either side of alignment spring 29 (depicted in FIG. 4) is connected to the plug valve alignment spring hook 16 and case alignment spring hook 37. The alignment spring 29 allows the center complex 36 to align correctly with the center of the middle case 27. As the activated complex 35 and the center complex 36 moves back and forward proximally and distally, the stopcock rotator 17 (displayed in FIGS. 8AB and 8B) automatically spins the stopcock 14 into/out of hole 12, which is shown in FIGS. 15A and 15B, and opens and closes the plug valve 6 to prevent contamination of the medication. This process makes sure no air bubbles, blood, or bacteria get into vial 13, thus also keeping the bellows 13B compressed after use. In this way, alignment spring 29 helps to precisely realign the now smaller vial 13.

If the user is still in shock 5-15 minutes after their first dose, they can flip the auto-injector around, and the same process will be repeated.

The invention is not limited to the above description. Other embodiments could make the invention more compact. Currently, one embodiment of the invention measures 5.5 inches in length and 1.5 inches in width. Other embodiments could be made at different scales, but determining the best size would rely on data collected from user testing. Manufacturers may produce individual parts on smaller or bigger scales using injection molding once the best form factor is established. In addition, the shape of the device could be changed to accommodate grooves for people to wrap their fingers around, making it more ergonomic.

Additionally, the prong-push system can be replaced by a set of buttons, for example. Each side of the auto-injector can have two buttons that must be squeezed to activate the high-force spring to inject the epinephrine (e.g., to push the lateral plunger(s) inward). In addition, the safety cap can be modified to cover the buttons (e.g., more cylindrical-shaped than a flat disc), so they are not pressed by mistake. In addition or in the alternative, a slider mechanism can be used as the ignition. The slider extends outside of the case and wraps around the circular body of the device. The user would push the slider 90 degrees to unlock the strong compressed spring, and then they would retract the needle themselves by pulling back a small retraction bar attached to the vial. Another embodiment could involve changing internal mechanisms. As described above, the bellow is held in place by two low-force springs, which also serve to help retract the needle. However, this can be changed to a single low-force spring, connected from the center of the casing to the center of the vial. When the vial is propelled distally upon injection, this centered spring will stretch and bring the vial back proximally into the centered position (which is possible once the high-force spring is disengaged from the vial).

As another option, the needle hole can be covered with a thin, transparent film (e.g., made of silicone) to prevent contamination even if the user removes the safety cap without needing to use the device (e.g., children sometimes remove it out of curiosity just to see how it looks like). This film is thin enough to be penetrated by the needle and will not affect the injection.

It should be understood that, in the context of this disclosure, "at least one of" followed by a series of elements means any one of the elements in the series or any combination of the elements in the series, including all of the elements. So, for example, a recitation of "at least one of A, B, or C" means any of A, B, C, A+B, A+C, B+C, or A+B+C.

Having described certain embodiments of the invention, it should be understood that the invention is not limited to the above description or the attached exemplary drawings. Rather, the scope of the invention is defined by the claims appearing hereinbelow and includes any equivalents thereof as would be appreciated by one of ordinary skill in the art.

What is claimed is:

1. A manual multi-dose auto-injector structured to manually dispense multiple discrete doses of a drug, comprising:
   a hollow housing having at least a first housing end and a second housing end;
   an at least partially compressible vial disposed in a central portion of said housing adapted to contain multiple doses of the drug to be dispensed, said vial in mechanical communication with said first housing end and said second housing end;

a first needle spring-biasedly disposed substantially in said first housing end in a first unactivated configuration and disposed at least partially protruding from said first housing end in a first activated configuration, said first needle manually selectively in fluid communication with said vial;

a second needle spring-biasedly disposed substantially in said second housing end in a second unactivated configuration and disposed at least partially protruding from said second housing end in a second activated configuration, said second needle manually selectively in fluid communication with said vial;

at least one case alignment spring hook formed on an inner surface of said housing;

a first activated complex onto which said first needle is secured;

a second activated complex onto which said second needle is secured;

at least one central alignment spring hook formed on at least one of said first activated complex or said second activated complex; and at least one alignment spring secured at a first spring end to said at least one case alignment spring hook and secured at a second spring end to said at least one central alignment spring hook, wherein pressing said first housing end against a user's body causes said first needle to move from said first unactivated configuration to said first activated configuration and compresses said vial to a first extent such that a first dose of said drug is dispensed from said first needle to the user, and wherein pressing said second housing end against a user's body causes said second needle to move from said second unactivated configuration to said second activated configuration and compresses said vial to a second extent such that a second dose of said drug is dispensed from said second needle to the user, and wherein said at least one alignment spring aligns at least one of said first activated complex or said second activated complex with said housing.

2. A manual multi-dose auto-injector structured to manually dispense multiple discrete doses of a drug according to claim 1, further comprising:

a first spring-biased collar engaging a first end of said vial, said first spring-biased collar being locked in a first proximal position via a first locking mechanism in said first unactivated configuration and pushed into a distal position in said first activated configuration when said first locking mechanism is unlocked; and a second spring-biased collar engaging a second end of said vial, said second spring- biased collar being locked in a second proximal position via a second locking mechanism in said second unactivated configuration and pushed into a distal position in said second activated configuration when said second locking mechanism is unlocked.

3. A manual multi-dose auto-injector structured to manually dispense multiple discrete doses of a drug according to claim 2, further comprising:

a first central spring biasing said first spring-biased collar; and a second central spring biasing said second spring-biased collar.

4. A manual multi-dose auto-injector structured to manually dispense multiple discrete doses of a drug according to claim 2, each of said first and second locking mechanisms respectively comprising:

an end ring disposed at the distal end of said housing end;

at least one prong proximally extending from said end ring towards said collar;

at least one radial plunger spring-biased into a locking space formed in said housing in said unactivated configuration and pushed into an activation space in said collar in said activated configuration, wherein pressing said housing end against a user's body causes said end ring to push a proximal prong end of said at least one prong proximally into contact with said at least one radial plunger, thereby pushing said at least one plunger out of said locking space in said housing and into said activation space in said collar.

5. A manual multi-dose auto-injector structured to manually dispense multiple discrete doses of a drug according to claim 4, each of said first and second locking mechanisms respectively further comprising:

at least one plunger retraction slot formed in said housing distally from said locking space, wherein after said dose is dispensed, said at least one radial plunger is spring-biased into said at least one plunger retraction slot, and said needle is in a deactivated configuration.

6. A manual multi-dose auto-injector structured to manually dispense multiple discrete doses of a drug according to claim 5, wherein said collar is spring-biased proximally and said needle is withdrawn proximally back into said housing in said deactivation configuration.

7. A manual multi-dose auto-injector structured to manually dispense multiple discrete doses of a drug according to claim 5, wherein said end ring remains proximally pushed in said deactivated configuration to provide a visual indication that the respective injection has occurred.

8. A manual multi-dose auto-injector structured to manually dispense multiple discrete doses of a drug according to claim 2, wherein said vial comprises a first compressible region corresponding to said first dose and a second compressible region corresponding to said second dose.

9. A manual multi-dose auto-injector structured to manually dispense multiple discrete doses of a drug according to claim 8, said first compressible region comprising first bellows structured to fold when compressed by said first spring-biased collar and thereby force said first dose out of said vial and said first needle, and said second compressible region comprising second bellows structured to fold when compressed by said second spring-biased collar and thereby force said second dose out of said vial and said second needle.

10. A manual multi-dose auto-injector structured to manually dispense multiple discrete doses of a drug according to claim 1, wherein after said first dose is dispensed, said first needle moves from said first activated configuration to a first deactivated configuration, and wherein after said second dose is dispensed, said second needle moves from said second activated configuration to a second deactivated configuration.

11. A manual multi-dose auto-injector structured to manually dispense multiple discrete doses of a drug according to claim 10, further comprising:

a first plug valve in communication with said first needle, said first plug valve causing said first needle to move to said first deactivated configuration after said first dose is dispensed; and a second plug valve in communication with said second needle, said second plug valve causing said second needle to move to said second deactivated configuration after said second dose is dispensed.

12. A manual multi-dose auto-injector structured to manually dispense multiple discrete doses of a drug according to claim 1, wherein said vial comprises a first compressible region corresponding to said first dose and a second compressible region corresponding to said second dose.

13. A manual multi-dose auto-injector structured to manually dispense multiple discrete doses of a drug according to claim 12, said first compressible region comprising bellows structured to fold when compressed and thereby force said first dose out of said vial and said first needle, and said second compressible region comprising bellows structured to fold when compressed and thereby force said second dose out of said vial and said second needle.

14. A manual multi-dose auto-injector structured to manually dispense multiple discrete doses of a drug according to claim 1, wherein said drug comprises epinephrine.

15. A manual multi-dose auto-injector structured to manually dispense multiple discrete doses of a drug, comprising:

a hollow housing having at least a first housing end and a second housing end;

an at least partially compressible vial disposed in a central portion of said housing adapted to contain multiple doses of the drug to be dispensed, said vial in mechanical communication with said first housing end and said second housing end, said vial comprising a first compressible region corresponding to said first dose and a second compressible region corresponding to said second dose;

a first needle spring-biasedly disposed substantially in said first housing end in a first unactivated configuration and disposed at least partially protruding from said first housing end in a first activated configuration, said first needle manually selectively in fluid communication with said vial;

a second needle spring-biasedly disposed substantially in said second housing end in a second unactivated configuration and disposed at least partially protruding from said second housing end in a second activated configuration, said second needle manually selectively in fluid communication with said vial;

a first spring-biased collar engaging a first end of said vial, said first spring-biased collar being locked in a first proximal position via a first locking mechanism in said first unactivated configuration and pushed into a distal position in said first activated configuration when said first locking mechanism is unlocked; and a second spring-biased collar engaging a second end of said vial, said second spring-biased collar being locked in a second proximal position via a second locking mechanism in said second unactivated configuration and pushed into a distal position in said second activated configuration when said second locking mechanism is unlocked;

said first compressible region comprising first bellows structured to fold when compressed by said first spring-biased collar and thereby force said first dose out of said vial and said first needle, and said second compressible region comprising second bellows structured to fold when compressed by said second spring-biased collar and thereby force said second dose out of said vial and said second needle;

a first plug valve in communication with said first needle, said first plug valve causing said first bellows to remain compressed after said first dose is dispensed; and a second plug valve in communication with said second needle, said second plug valve causing said causing said second bellows to remain compressed after said second dose is dispensed, wherein pressing said first housing end against a user's body causes said first needle to move from said first unactivated configuration to said first activated configuration and compresses said vial to a first extent such that a first dose of said drug is dispensed from said first needle to the user, and wherein pressing said second housing end against a user's body causes said second needle to move from said second unactivated configuration to said second activated configuration and compresses said vial to a second extent such that a second dose of said drug is dispensed from said second needle to the user.

* * * * *